United States Patent
Harpaz et al.

(10) Patent No.: US 10,512,760 B2
(45) Date of Patent: Dec. 24, 2019

(54) CERVICAL CANAL DILATION DEVICE

(71) Applicant: AQUEDUCT MEDICAL LTD., Nazareth Illit (IL)

(72) Inventors: Omer Harpaz, Kibbutz Yizrael (IL); Amnon Weichselbaum, Haifa (IL)

(73) Assignee: AQUEDUCT MEDICAL LTD., Nazareth Illit (IL)

( * ) Notice: Subject to any disclaimer, the term of this patent is extended or adjusted under 35 U.S.C. 154(b) by 43 days.

(21) Appl. No.: 15/319,784

(22) PCT Filed: Apr. 30, 2015

(86) PCT No.: PCT/IL2015/000020
§ 371 (c)(1),
(2) Date: Dec. 18, 2016

(87) PCT Pub. No.: WO2016/001911
PCT Pub. Date: Jan. 7, 2016

(65) Prior Publication Data
US 2017/0143944 A1    May 25, 2017

Related U.S. Application Data

(60) Provisional application No. 62/018,609, filed on Jun. 29, 2014.

(51) Int. Cl.
*A61M 25/10*    (2013.01)
*A61M 29/02*    (2006.01)
*A61M 31/00*    (2006.01)

(52) U.S. Cl.
CPC ........ *A61M 25/1011* (2013.01); *A61M 29/02* (2013.01); *A61M 31/00* (2013.01);
(Continued)

(58) Field of Classification Search
CPC .......... A61M 25/1011; A61M 25/1002; A61M 25/104; A61M 25/10; A61M 25/1018; A61M 25/10181; A61M 2025/1052; A61M 2025/1013; A61M 2025/105; A61M 29/02; A61M 16/0481; A61M 16/04; A61M 2210/1433; A61B 17/0218; A61B 17/22; A61B 17/42; A61B 17/12136; A61B 17/4241; A61B 17/7065; A61B 17/12045; A61B 17/12186; A61B 2017/00557; A61B 2017/0256; A61B 2017/22054; A61B 2017/22062; A61B 2017/22055
See application file for complete search history.

(56) References Cited

U.S. PATENT DOCUMENTS 4,423,725 A * 1/1984 Baran .................. A61B 17/22
128/207.15
4,693,704 A    9/1987 Ogita
(Continued)

FOREIGN PATENT DOCUMENTS

WO    WO2004052185    11/2004
WO    WO2006128194    11/2006

*Primary Examiner* — Ryan J. Severson
*Assistant Examiner* — Mohamed G Gabr
(74) *Attorney, Agent, or Firm* — Mark M. Friedman

(57) ABSTRACT

The cervical canal dilation device of the present invention relates to controlled injection of liquid or gel to the cervical canal in order to obtain a desired predetermined dilation while causing the treated woman minimal discomfort. The injection of a substance having a liquid or gel characteristics into the cervical canal is done while the inner and outer orifices (internal os and external os) of the canal are sealed by two reversibly inflatable balloons, referred to as the "dilating balloons". An inflatable balloon at the tip or near the tip of the cervical canal dilation device anchors the device (in the uterine cavity linked to the internal os) to the desired position in the cervix canal for the dilation treatment. The amount of fluid or gel injected into the cervix canal can be calculated apriori to expand the width of the canal to the desired dimension.

7 Claims, 5 Drawing Sheets

(52) U.S. Cl.
CPC .............. *A61M 2025/1015* (2013.01); *A61M 2025/1052* (2013.01); *A61M 2025/1081* (2013.01)

(56) References Cited

U.S. PATENT DOCUMENTS

| | | | | |
|---|---|---|---|---|
| 4,976,692 | A | * 12/1990 | Atad | .................. A61M 25/1011 604/101.03 |
| 5,722,983 | A | 3/1998 | Van Der Weegen | |
| 6,287,320 | B1 | * 9/2001 | Slepian | ............... A61L 24/0031 604/101.05 |
| 2002/0111602 | A1 | 8/2002 | Ackerman | |
| 2004/0153116 | A1 | * 8/2004 | Nobles | ..................... A61B 1/32 606/193 |
| 2006/0058831 | A1 | * 3/2006 | Atad | ................. A61M 25/1002 606/193 |
| 2007/0288051 | A1 | * 12/2007 | Beyer | ................... A61M 29/02 606/193 |
| 2010/0145224 | A1 | * 6/2010 | Lee | ....................... A61M 25/10 600/562 |
| 2013/0096499 | A1 | * 4/2013 | Tchirikov | ........... A61B 17/0057 604/101.05 |

\* cited by examiner

CERVICAL CANAL DILATION DEVICE

FIELD OF THE INVENTION

The present invention relates to a device for performing cervical canal dilations. More specifically, the cervical canal dilation device of the present invention relates to injecting liquid or gel substance to the cervix canal while the canal orifices (internal os and external os) are reversibly sealed, causing a predetermined dilation width.

BACKGROUND OF THE INVENTION

The terms "distal" and "proximal" in the context of the present text refer to the direction of the end-portions of the dilation device positioned in the cervix canal in regards to the inner and outer orifices of the cervix canal, respectively.

Approximately 3 million cervical canal dilations are performed annually in the United States for the purpose of intra-uterine procedures. These procedures include: abortions, hysteroscopies and other curettages. Cervical canal dilation allows medical practitioners greater access to the inside of the uterus in order to insert surgical tools for the completion of intra-uterine procedures.

Presently there are primarily two mechanical techniques for dilating the cervix. The first technique is the insertion of Laminaria (dry, sterile seaweed) or synthetic osmotic dilators into the cervix. When either Laminaria or a synthetic osmotic dilators come into contact with body fluids, it expands and enlarges the opening of the cervix. Often, this process requires two patient-visits and approximately 10-12 hours for sufficient dilation to occur.

The second technique, referred to as Hegar dilation, involves the insertion and removal of metal rods that are graduated in increasing diameter. This process is painful, requires the use of anesthesia, and is associated with a risk of uterine and cervix damage and cervical incompetence.

In addition to the two primarily cervix dilating techniques mentioned above there are techniques in which cervix dilating is achieved by the use of inflated balloons.

In U.S. patent application 2007/0288051 Beyer et al. disclose a cervical canal dilator device in which an elongate tubular or cylindrical shaft is inserted into the cervix canal. The shaft is provided with internal cavities that communicate with several dilation-balloons in such a manner as to permit the separate inflation of the balloons. A balloon is positioned on the distal end of the shaft and anchors the dilator against the bottom of the cervix when inflated after the dilator is inserted in a cervix and the remaining dilation balloons being positioned between the distal and proximal ends so as to effect optimum dilation of the cervical canal when inflated.

In PCT publication WO2004/052185 Foltz et al. disclose a cervical canal dilating device and method that includes a plastic shaft, and two inflatable members. The shaft can range from being rigid to being highly flexible. One of the inflatable members is fabricated of a non-elastic material and is configured to have a maximum inflatable diameter. The second inflatable member is configured to have a predetermined maximum inflatable diameter. A control system includes means for measuring pressure configured for at least monitoring the pressure of the second inflatable member. In deploying, the dilating device is inserted into the cervical canal. The first inflatable member is expanded in the uterus. The second inflatable member is positioned in the cervical canal and gradually inflated to a predetermined maximum diameter.

The mentioned cervix dilating devices are cumbersome to use and do not give the professional operator the ability to readily adjust the procedure to the physiological requirement of any individual treated woman.

The use of inflated balloons for the sealing of the cervix canal is described in the devices disclosed in the U.S.-patent and U.S. patent application given below:

In U.S. Pat. No. 4,976,692 Atad discloses a device in which two distantly positioned balloons are connected to a catheter that is inserted into the cervix canal. When the catheter is inserted the balloons are inflated so as to cover and seal the internal and external opening of the cervix canal. An opening located between the balloons enables confined input of medical gel or solution through catheter into the cervix canal. Atad's device relates to widening of the cervix canal prior to birth giving and does not relate and is not able to preform controlled cervical canal dilation procedures in treated patients.

In U.S. patent application 2002/0111602 Ackerman et al. discloses a non-surgical catheter device for entry into a uterus. The device includes an elongated balloon that is inserted into the cervical canal of the uterus and a tube that extends through the balloon from the eternal opening of the cervix to the internal opening of the cervix and into the uterus. By inflating the balloon, the two sections extending from the cervical canal increase in size and seal the passage through the canal. Through an opening adjacent to or at the end of the tube diagnostic fluid is dispensed into the uterus. Ackerman's device relates to uterus medical treatment procedures and does not relate to and is not able to perform controlled cervical canal dilation procedures in treated patients.

The cervical canal dilator of the present invention provides a friendly to use solution that overcomes the above mention disadvantages of the current dilators and enables controlled radial dilation of the cervix (to a predetermined diameter) within a few minutes.

SUMMARY OF THE INVENTION

The cervical canal dilation device of the present invention relates to controlled injection of liquid or gel to the cervical canal in order to obtain a desired predetermined dilation while causing the treated woman minimal discomfort. The injection of a substance having a liquid or gel characteristics into the cervical canal is done while the inner and outer orifices (internal os and external os) of the canal are sealed by two reversibly inflatable balloons, referred to as the "dilating balloons". An inflatable balloon at the tip or near the tip of the cervical canal dilation device anchors the device (in the uterine cavity linked to the internal os) to the desired position in the cervix canal for the dilation treatment. The amount of fluid or gel injected into the cervix canal can be calculated apriori to expand the width of the canal to the desired dimension.

All components of the cervical canal dilation device of the present invention are made of medical approved materials. More so, the assembly of components of the cervical canal dilation device of the present invention that come into contact with body of the treated patient are presently sold on the market and have been approved for medical use by authorized agencies such as the FDA and the EC authorities.

The balloons used in cervical canal dilation device can be (but not limited) produced by the Vention Medical Company (see: http://www.ventionmedical.com/products-and-services/advanced-polymers/medical-balloons)./

Tubes used in cervical canal dilation device are typically made of a soft and flexible material such as, but not limited to, silicone, rubber, Nylon, PET, various polyethylenes and soft plastic materials.

The present invention is cervical canal dilator device constructed of: a hollow rod shaft component, sealed at its proximal end, three elongated tubes, three tube connection ports, and three reversibly inflatable balloons.

Two of the three reversibly inflatable balloons are consecutively wrapped around the hollow rod in the proximal portion of the hollow shaft rod with a perforated segment of the shaft located between the two balloons. Optionally, the balloon of the two balloons positioned on the distal side of the hollow rod is made of a transparent material, typically, but not necessarily, of plastic material. The portion of the hollow shaft that is wrapped by the transparent-material balloon has graduated markings along the shaft. The perforated hollow rod shaft segment is connected to the neighboring sections of the hollow rod shaft but does not communicate with the balloons or the neighboring hollow rod shaft sections. Alternatively, the perforated segment of the hollow rod shaft is a separate perforated tube which is connected to and does not communicate with the hollow rod shaft sections. Typically, the two balloons have a cylindrical configuration when inflated.

One of the elongated tubes is inserted through the hollow rod shaft and is connected and communicates freely with the two reversibly inflatable balloons in the proximal portion of the hollow rod shaft. The elongated tubes is connected in the distal portion of the hollow rod shaft and communicates freely with one of the connection ports.

The third reversibly inflatable balloon is connected towards the end of the proximal portion of the hollow rod shaft, and the balloon is connected and communicates freely with the second of the elongated tubes, which is inserted through the hollow rod shaft. The elongated tube is connected in the distal portion of the hollow rod shaft, and communicates freely with, the second of the connection ports, The third of the elongated tubes is connected and communicates freely with the perforated segment of the hollow rod shaft. The elongated tube is connected in the distal portion of the hollow rod shaft and communicates freely with, the third of the connection ports.

When deployed, an optional protective sleeve that covers the inflatable balloons is slid away and the hollow rod shaft is inserted into a cervical canal and the uterine cavity.

The procedure of deployment of the cervical canal dilator device of the present invention: The two balloons wrapped around the hollow rod shaft are inflated via the elongated tube and the connection port by pressurized liquid or gas, so as to seal the two orifices (the term "orifice" interchangeably abbreviates to "os") of the cervical canal (internal os and external os). The third reversibly inflatable balloon is inflated, also using pressurized liquid or gas, inside the uterine cavity via the elongated tube and the connection port. The third balloon is inflated to anchor the hollow rod shaft in the uterine cavity and the cervical canal. A predetermined volume of dilating substance is injected into the cervical canal via the connection port and the elongated tube and through the perforated segment of hollow rod shaft. The dilating substance can have either a liquid or gel characteristics. The dilating substance causes a predetermined dilating width dilation of the cervical canal in correlation with the volume of dilating substance is injected into the cervical canal. The optional graduated markings along the shaft facilitate better control of fine adjustments in the sealing of the cervical canal of the treated patient by the device of the present invention by enabling the exact monitoring of the distances of insertion and withdrawal of the device from the patient.

After the medical treatment the three reversibly inflatable balloons are deflated, the dilating substance freely flows out of the cervical canal and the hollow rod shaft withdrawn from the cervical canal. Optionally, the protective sleeve is slid over the reversibly inflatable balloons and the hollow rod shaft withdrawn from the cervical canal.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF AN EMBODIMENT

Figure 1:
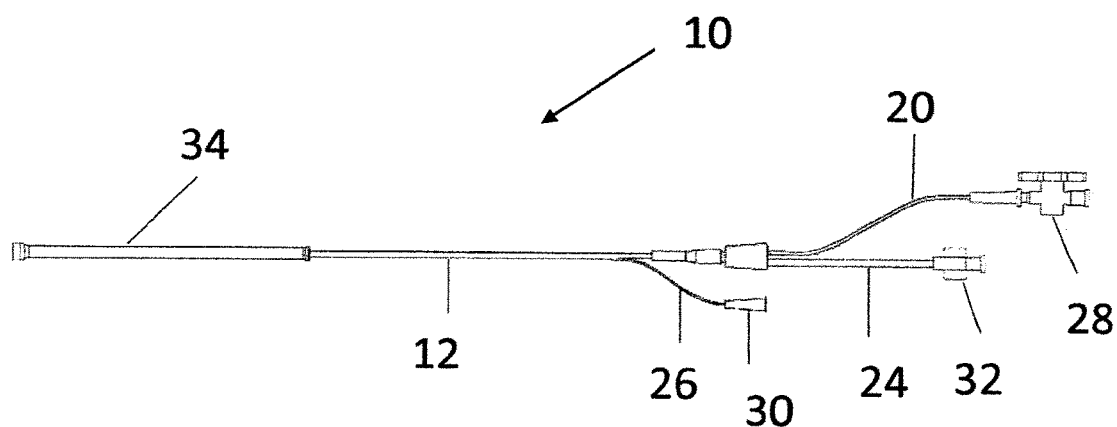
FIG. 1 illustrates an embodiment of a cervical canal dilation device of the present invention, shown with the end portion of its proximal side covered by a protection sleeve.

Reference is presently made to the construction of an embodiment of a cervical canal dilation device in accordance to the present invention:

The cervical canal dilation device (10) of the present invention is constructed of a hollow rod shaft, referred from here after in the text as a "shaft" (12), typically made of (but not limited to) rigid plastic material. The terms "proximal" "distal" in reference to cervical canal dilation device of the present invention relate to the end-side of the shaft that is inserted into the cervix canal when the device is deployed and to the opposite side-end, respectively. In the distal edge-portion of shaft (12) two inflatable dilating balloons, typically, cylinder-shaped (designated: 14 and 16) are wrapped around shaft (12). Optionally, balloon (16) is made of a transparent material, typically but not necessarily, of plastic material. The portion of the hollow shaft wrapped by balloon (16) has graduated markings along the shaft, designated (15). A perforated segment (17) with at least one fluid injection pore (18) is located along shaft (12) and between dilating balloons (14) and (16). Typically, the perforated segment is a perforated tube connected on both neighboring sides to shaft (12) but does not communicate with the shaft. Near or at the tip of the distal side of shaft (12), a frontal-restriction-balloon (22) is connected to the shaft. Three tubes run through the length of shaft (12): tube (20) for inflation of dilating balloons (14) and (16); tube (24) for inflation of frontal-restriction-balloon (22) and tube (26) for injecting a dilating fluid or gel substance that pours from pore(s) (18) into the cervical canal. The tubes are connected and communicate freely with the three inflatable balloons and with the perforated segment (17). Tubes (20), (24) and (26) each connect and communicate freely with a connection-port, designated (28), (30) and (32), respectively, at their proximal end-side. Connection-ports (28) and (30) enable the connection of the tubes to a source of compressed liquid and or compressed gas for inflating balloons (14), (16) and (22), respectively. Connection-port (32) typically enables the connection to a syringe for the injecting a dilating fluid or gel substance into tube (26). A protective-sleeve (34) covers dilating balloons (14) and (16) and frontal-restriction-balloon (22) when the cervical canal dilation device (10) of the present invention is in storage and prior to deployment and the three balloons deflated.

Figure 2:
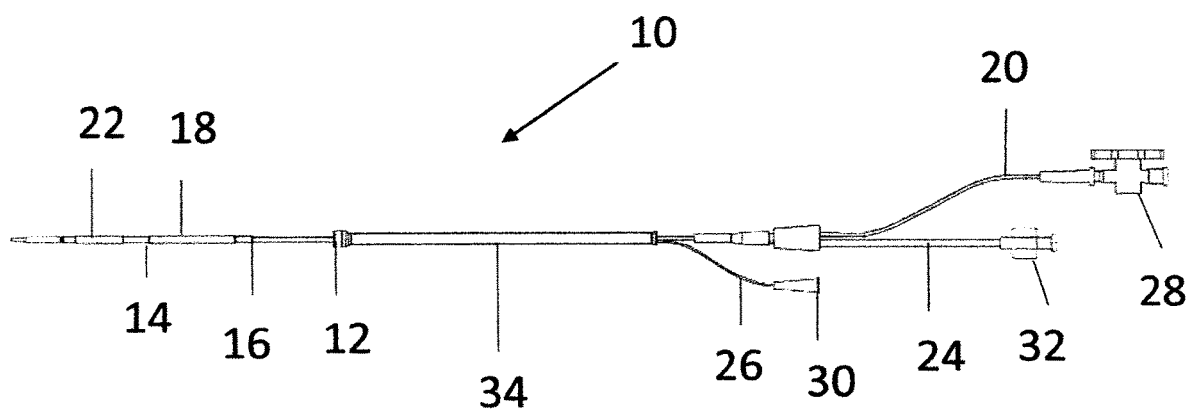
FIG. 2 illustrates the embodiment of the cervical canal dilation device shown FIG. 1, with deflated restriction and dilating balloons exposed after the sliding of the protection sleeve.

Reference is currently made to FIGS. 1 to 3, which illustrate the configurational changes of the restriction and dilating balloons in the course of deploying the cervical canal dilation device of the present invention.

In storage, prior to deployment, the end portion of the proximal side of the shaft (12) of the cervical canal dilation device of the present invention, is covered by a protective-sleeve (34), as illustrated in FIG. 1.

In preparation for deployment, protective-sleeve (34) is slid over shaft (12) towards the proximal side of shaft (12), thus exposing dilating balloons (14) and (16) and frontal-restriction-balloon (22), all three balloons being in a deflated configuration, as illustrated in FIG. 2.

Figure 3A:
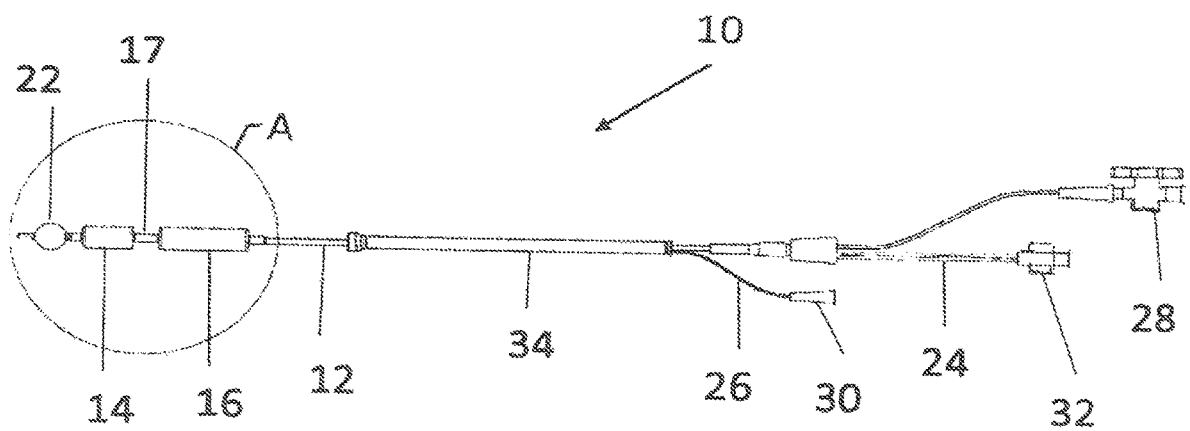
FIG. 3A illustrates the embodiment of the cervical canal dilation device shown FIG. 2, with restriction and dilating balloons inflated.
Figure 3B:
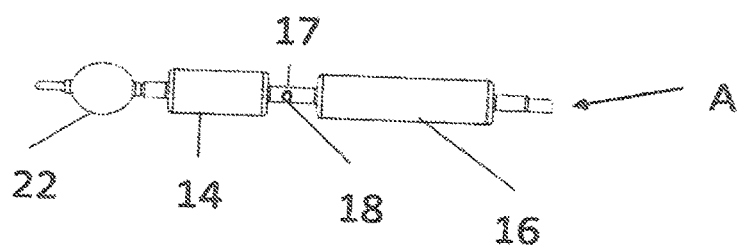
FIG. 3B illustrates a blown-up section of the cervical canal dilation device shown FIG. 3, showing in detail the inflated restriction and dilating balloons.

When the dilating balloons (14) and (16), is deployed in the cervical canal the dilating balloons (14) and (16) and frontal-restriction-balloon (22) are inflated, as illustrated in FIG. 3A. FIG. 3B illustrates a blowup section of FIG. 3A (the section designated: A) showing a detailed view of dilating balloons (14) and (16), frontal-restriction-balloon (22) and tube (17) with injection pore (18) between dilating balloons (14) and (16).

Reference is presently made to FIGS. 4 to 9 which illustrate a partial crosscut view of the reproductive organs of a human female, showing the upper inner-body section of the vagina, the cervix canal region and the region of entrance from the cervix canal to the uterus. The Figures illustrate consecutive stages of deployment of the cervical canal dilation device of the present invention in the cervix canal of a treated patient.

Figure 4:
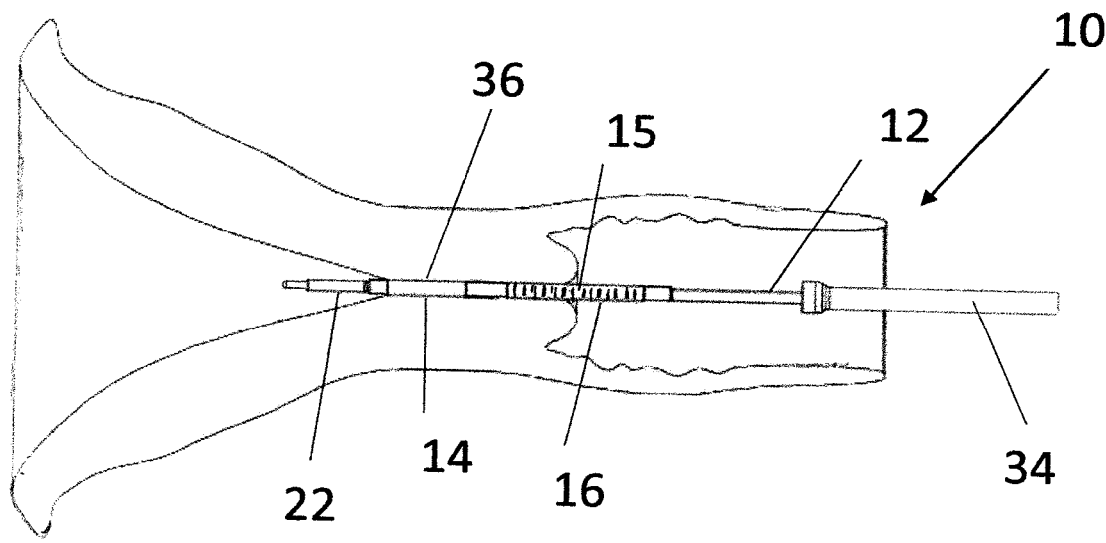
FIG. 4 illustrates an embodiment of the cervical canal dilation device of the present invention shown in FIG. 2, in the first stage of being deployed in the cervix canal of a patient. Only a proximal section of the device, inserted into cervix canal and uterine cavity, is shown in the figure.

In the first stage of deployment of the cervical canal dilation device (10) of the present invention, illustrated in FIG. 4, protective-sleeve (34) is slid from the end portion of the proximal side of the shaft (12) towards the distal side of shaft (12) and shaft (12) is inserted into the cervix canal (36).

Figure 5:
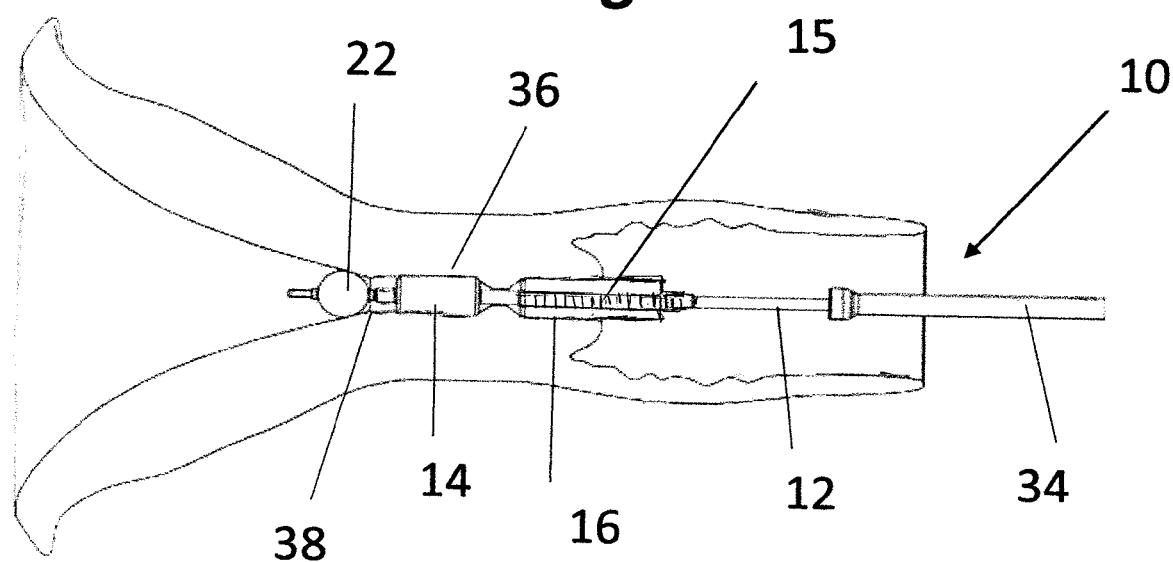
FIG. 5 illustrates the cervical canal dilation device shown in FIG. 4, in the second stage of being deployed in the cervix canal of a patient, with dilating balloons in the cervix canal and a frontal-restriction-balloon inflated inside the uterine cavity.

In the second stage of deployment, shown in FIG. 5, frontal-restriction-balloon (22) is inflated by introducing pressurized gas or liquid into the balloon through port (30) and via tube (24). With balloon (22) inflated, shaft (12) is gently withdrawn from the cervix canal till the frontal-restriction-balloon (22) stops the withdrawing movement by pressing against the rim of the inner-body orifice of the cervix canal (38). With frontal-restriction-balloon (22) position at the orifice of the cervix canal (38), dilating balloons (14) and (16) are gradually inflated up to 6 atmospheres and during several (typically 5) minutes by introducing pressured pressurized gas or liquid into the balloons (by using a syringe or pressure-gage inflator) through port (28) and via tube (20). Ports (28) and (30) and tubes (20) and (24) are illustrated in FIG. 3A. The inflation of balloons (14) and (16) in cervix canal (38) seals the inner and outer body entrances of the cervix canal (38) while increasing the width of the cervix canal (38) in accordance with the extent of the inflation of the balloons, as illustrated in the figure. The optional graduated markings (15) along shaft (16) facilitate better sealing control of the cervical canal of the treated patient by enabling the exact monitoring of the distances of insertion and withdrawal of cervical canal dilator device into the body of the patient. The graduated markings (15) are seen through the transparent wall of inflated balloon (16), as shown in FIG. 5.

Figure 6:
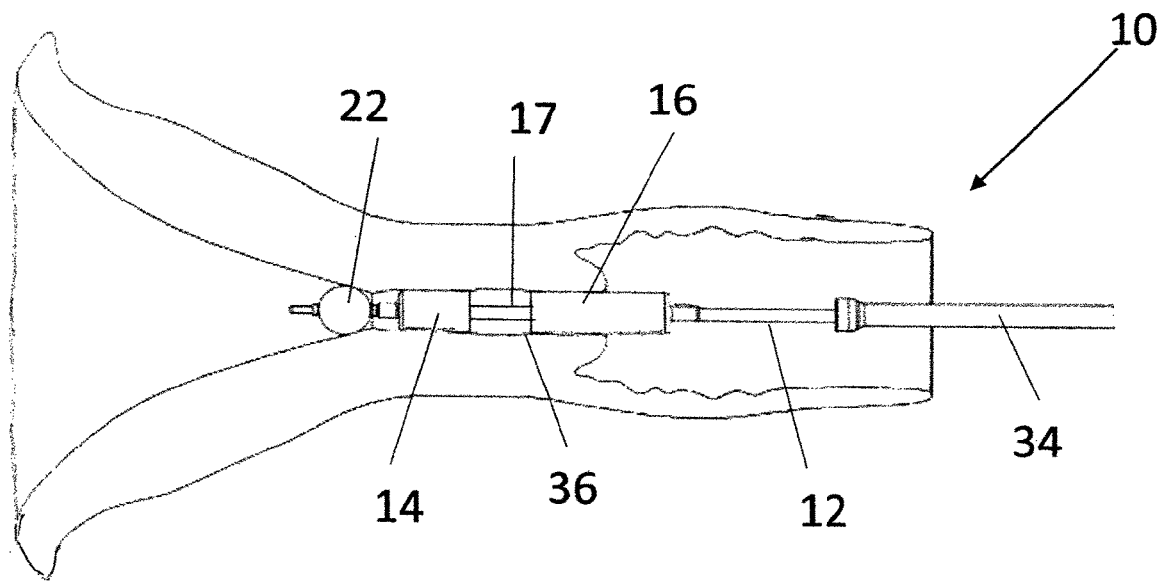
FIG. 6 illustrates the cervical canal dilation device shown in FIG. 4, in the third stage of being deployed in the cervix canal of a patient with the frontal balloon inside the uterine cavity and dilating fluid injected into the cervix canal, between the two dilating balloons in the cervix canal.

In the third stage of deployment, shown in FIG. 6, pressurized liquid is injected into tube (26) via port (32). The pressurized liquid pours out of tube (26) through injection pore (18) located in tube segment (17), between frontal-restriction-balloon (22), typically, but necessarily, having a spherical configuration. Tube segment (17) and injection pore (18) are illustrated in FIG. 3B. The injected fluid gradually expands the volume entrapped in the cervix canal (36) thus increasing the width of the canal to a desired dimension.

Figure 7:
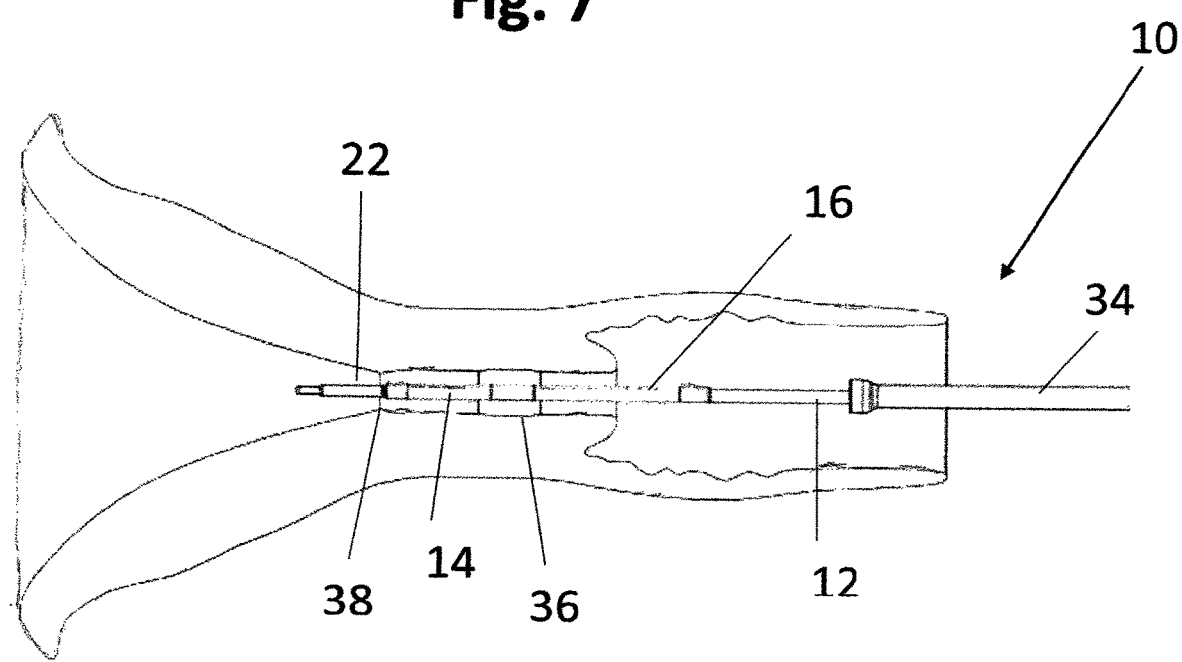
FIG. 7 illustrates the cervical canal dilation device shown in FIG. 4, in the fourth stage of being deployed in the cervix canal of a patient, with dilating fluid removed from the cervix canal and the dilating balloons and a frontal-restriction-balloon deflated.

In the fourth stage of deployment, shown in FIG. 7, dilating balloons (14) and (16) are gradually deflated through tube (20) and port (28). With dilating balloons (14) and (16) deflated, the entrapped liquid freely flows out of the cervix canal (36) through the outer-body orifice of the canal. Following the deflation of balloons (14) and (16) frontal-restriction-balloon (22) is deflated through tube (24) and port (30). After the three balloons are deflated the cervix canal (36) remains open at both its orifices and the cervical canal and the orifices remain with a desired increased width for a considerable time period. The increased width allows the performance of medical treatment procedures to be carried out through the expanded canal.

Figure 8:
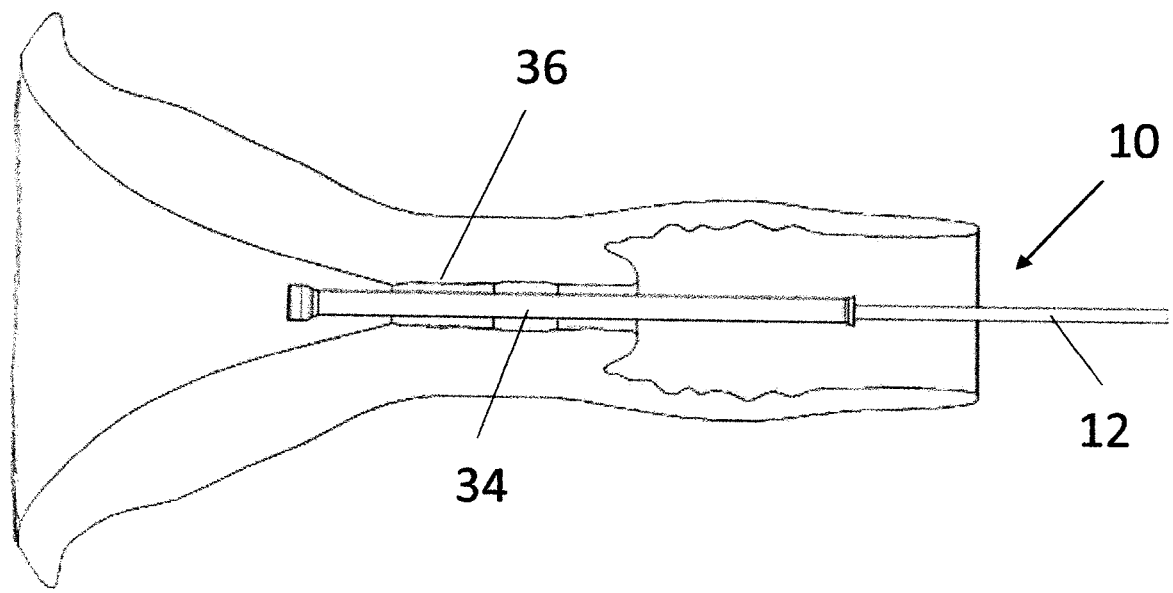
FIG. 8 illustrates the cervical canal dilation device shown in FIG. 4, in the fifth stage of being deployed in the cervix canal of a patient, after the dilating of the cervix canal and with a protective sleeve cover re-placed on the proximal end side of the device, as shown in FIG. 1.
Figure 9:
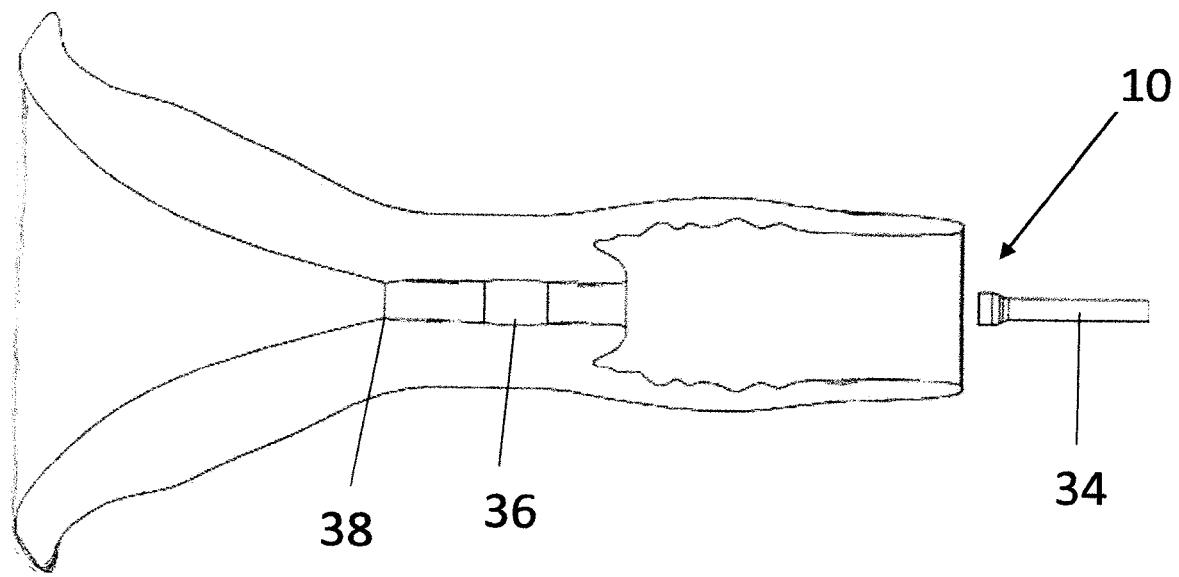
FIG. 9 illustrates the cervical canal dilation device shown in FIG. 4, in the sixth stage of being deployed in the cervix canal of a patient, after the device has been withdrawn from the cervix canal of the treated patient and the cervix canal remaining dilated.

In the fifth and sixth stages of deployment, shown in FIG. 8 and FIG. 9, protective-sleeve (34) is slid over shaft (12) in the proximal direction and re-covers deflated dilating balloons (14) and (16) frontal-restriction-balloon (22). The covering of the balloons is done to ensure the smoothness of the surface shaft (12), thus minimizing the scratching of the wall of the cervix canal (36) upon withdrawing the shaft (12) from the cervical canal (36). Shaft (12) is withdrawn from the cervical canal (36) while the canal remains dilated.

What is claimed is:

1. A cervical canal dilator device comprising:
   a hollow rod shaft having proximal and distal ends, wherein said hollow rod shaft is sealed at its proximal end,
   three reversibly inflatable balloons formed along said shaft; and
   three elongated tubes extending internally along said shaft, wherein a first of said tubes is connected to a first and second of said balloons for inflation thereof, wherein a second of said tubes is connected to a third of said balloons, each of said first and second tubes having a connection port on said distal end of said shaft;
   wherein said hollow rod shaft has a perforated segment that does not communicate with the neighboring sections of said hollow rod shaft,
   wherein said first and second of said three balloons are consecutively wrapped around said hollow rod shaft in its proximal portion, said perforated segment being located between said first and second balloons and not communicating with said first and second balloons,
   wherein the third of said three balloons is connected towards the end of said proximal portion of said hollow rod shaft and communicates freely with the second of said tubes, said second tube being connected in the distal portion of said hollow rod shaft and communicating freely with the second of said connection ports,
   wherein the third of said tubes is connected and communicates freely with said perforated segment, said third tube being connected in the distal portion of said hollow rod shaft and communicates freely with the third of said connection ports,
   wherein said hollow rod shaft is insertable into a cervical canal, and said first and second balloons are simultaneously inflated via said first tube and said first connection port so as to seal the two orifices of the cervical canal, said first and second balloons being capable of inflation to a pressure of approximately 6 atmospheres,
   wherein said third balloon is capable of being inflated inside the uterine cavity for enabling anchoring of said hollow rod shaft to the cervical canal,
   and wherein a predetermined volume of pressurized liquid is configured to be injected into the cervical canal via said third connection port and third tube and through the perforated segment of said hollow rod shaft,
   thereby said predetermined volume of pressurized liquid exiting said perforated segment of said hollow rod shaft expands the volume of liquid in the cervical canal, thereby dilating the cervical canal, said shaft then being removed from the patient after the cervical canal has been dilated.

2. The device according to claim 1 wherein said perforated segment of said hollow rod shaft has a perforated tube connected to said hollow rod shaft.

3. The device according to claim 1 wherein said first and second reversibly inflatable balloons have a cylindrical configuration when inflated.

4. The device according to claim 3 wherein a balloon of the first and second balloons that is positioned on a distal side of said hollow rod shaft is made of a transparent material.

5. The device of claim 1 wherein said distal portion has graduated markings along said shaft.

6. The device according to claim 1 wherein said pressurized liquid has liquid characteristics.

7. The device according to claim 1 wherein said pressurized liquid has gel characteristics.

* * * * *